US010039263B2

(12) United States Patent
Teychene et al.

(10) Patent No.: US 10,039,263 B2
(45) Date of Patent: Aug. 7, 2018

(54) UNIT FOR MARKING AND/OR SAMPLING ANIMAL TISSUE AND CORRESPONDING MARKING AND/OR SAMPLING TOOL

(75) Inventors: Bruno Teychene, Mouzieys-Teulet (FR); Jean-Jacques Hilpert, Vitre (FR)

(73) Assignee: Allflex Europe (FR)

( * ) Notice: Subject to any disclaimer, the term of this patent is extended or adjusted under 35 U.S.C. 154(b) by 977 days.

(21) Appl. No.: 13/812,817

(22) PCT Filed: Jun. 23, 2011

(86) PCT No.: PCT/EP2011/060558
§ 371 (c)(1),
(2), (4) Date: Apr. 29, 2013

(87) PCT Pub. No.: WO2012/013429
PCT Pub. Date: Feb. 2, 2012

(65) Prior Publication Data
US 2013/0211416 A1    Aug. 15, 2013

(30) Foreign Application Priority Data

Jul. 30, 2010    (FR) ..................... 10 56349

(51) Int. Cl.
*A61B 17/00* (2006.01)
*A01K 11/00* (2006.01)
(Continued)

(52) U.S. Cl.
CPC ............ *A01K 11/00* (2013.01); *A01K 11/001* (2013.01); *A01K 11/002* (2013.01);
(Continued)

(58) Field of Classification Search
CPC ... A01K 11/001–11/003; A01K 13/003; A61B 10/0026; A61B 17/3417;
(Continued)

(56) References Cited

U.S. PATENT DOCUMENTS

| 42,188 A | 4/1864 | Hamilton |
| 1,347,868 A | 7/1920 | Nichols |

(Continued)

FOREIGN PATENT DOCUMENTS

| EP | 1014861 A1 | 7/2000 |
| EP | 1024354 A1 | 8/2000 |

(Continued)

OTHER PUBLICATIONS

International Search Report and Written Opinion for International Application PCT/EP2011/060558, dated Aug. 19, 2011, 9 pgs.
(Continued)

*Primary Examiner* — Diane Yabut
*Assistant Examiner* — Erich Herbermann
(74) *Attorney, Agent, or Firm* — KPPB LLP

(57) ABSTRACT

The invention relates to a unit for marking and/or sampling animal tissue, including a male portion (12) for marking and/or sampling tissue, and a female portion (13) for marking and/or receiving said tissue. According to the invention, such a unit includes an intermediate element (14) for connecting said male and female portions together, said intermediate connection element (14) having a first portion (141) for rigidly connecting to said male portion and a second portion (192) for rigidly connecting to said female portion, enabling said male and female portions to be supported along a single marking and/or sampling axis (AA1) before marking and/or sampling said animal tissue, wherein the intermediate connection element is releasable.

13 Claims, 9 Drawing Sheets

(51) Int. Cl.
*A01K 13/00* (2006.01)
*A61B 10/02* (2006.01)

(52) U.S. Cl.
CPC .......... *A01K 11/003* (2013.01); *A01K 13/003* (2013.01); *A61B 10/0266* (2013.01)

(58) Field of Classification Search
CPC .............. A61B 17/3496; A61B 17/322; A61B 2017/32113; A61B 2017/3225; A61B 5/1411; A61B 5/15142
USPC ........ 606/117, 188, 184, 116, 186, 119, 167, 606/185, 181, 132; 40/300, 301; 600/562; 604/192, 198; 72/409.13; 227/143; 81/418, 44
See application file for complete search history.

(56) References Cited

U.S. PATENT DOCUMENTS

| | | | |
|---|---|---|---|
| 2,570,048 | A | 10/1951 | Cooke et al. |
| 2,617,359 | A | 11/1952 | Horn et al. |
| 2,749,566 | A | 6/1956 | Thomas |
| 3,731,414 | A | 5/1973 | Murphy et al. |
| 3,893,813 | A * | 7/1975 | Johnson .................... B01L 9/50 24/504 |
| 3,952,438 | A * | 4/1976 | Propst ....................... G09F 3/12 40/300 |
| 4,014,748 | A | 3/1977 | Spinner et al. |
| 4,021,952 | A | 5/1977 | Brierley |
| 4,185,635 | A | 1/1980 | Burford et al. |
| 4,206,757 | A | 6/1980 | Grandadam et al. |
| 4,359,015 | A | 11/1982 | Ritchey |
| 4,425,874 | A | 1/1984 | Child |
| 4,653,208 | A | 3/1987 | Wassilieff et al. |
| 4,694,781 | A | 9/1987 | Howe et al. |
| 4,878,456 | A | 11/1989 | Howe |
| 4,885,855 | A | 12/1989 | Marks et al. |
| 4,932,953 | A * | 6/1990 | Cohr .................... A01K 11/002 606/117 |
| 5,005,433 | A | 4/1991 | Patton et al. |
| 5,016,369 | A | 5/1991 | Parry |
| 5,156,160 | A | 10/1992 | Bennett et al. |
| 5,189,986 | A | 3/1993 | Burkoth |
| 5,268,148 | A | 12/1993 | Seymour |
| 5,388,588 | A | 2/1995 | Nabai et al. |
| 5,423,793 | A | 6/1995 | Isono et al. |
| 5,482,008 | A | 1/1996 | Stafford et al. |
| 5,526,822 | A | 6/1996 | Burbank et al. |
| 5,902,280 | A | 5/1999 | Powles et al. |
| 6,070,593 | A | 6/2000 | Chase |
| 6,080,173 | A | 6/2000 | Williamson et al. |
| 6,098,324 | A | 8/2000 | Nepote |
| 6,145,225 | A * | 11/2000 | Ritchey ................ A01K 11/002 40/300 |
| 6,164,501 | A | 12/2000 | Stradella |
| 6,196,978 | B1 | 3/2001 | Weilandt et al. |
| 6,255,101 | B1 | 7/2001 | Rousseau et al. |
| 6,382,827 | B1 | 5/2002 | Gebrian |
| 6,509,187 | B2 | 1/2003 | Brem |
| 6,659,338 | B1 | 12/2003 | Dittmann et al. |
| 6,708,432 | B2 | 3/2004 | Haar et al. |
| 6,968,639 | B2 | 11/2005 | Destoumieux |
| 7,198,629 | B2 | 4/2007 | Brem |
| 7,235,055 | B2 | 6/2007 | Pfistershammer |
| 8,517,957 | B2 | 8/2013 | Decaluwe et al. |
| 8,668,655 | B2 | 3/2014 | Destoumieux et al. |
| 8,906,310 | B2 | 12/2014 | Bonecker |
| 9,038,293 | B2 | 5/2015 | Decaluwe et al. |
| 9,301,497 | B2 | 4/2016 | Decaluwe et al. |
| 2002/0066418 | A1 | 6/2002 | Fearing et al. |
| 2002/0118595 | A1 | 8/2002 | Miller et al. |
| 2002/0160428 | A1 | 10/2002 | Sundrehagen |
| 2003/0093009 | A1 | 5/2003 | Newby et al. |
| 2004/0103567 | A1 | 6/2004 | Destoumieux |
| 2004/0167429 | A1 | 8/2004 | Roshdieh et al. |
| 2004/0242960 | A1 | 12/2004 | Orban, III et al. |
| 2005/0051109 | A1 | 3/2005 | Fantin et al. |
| 2005/0155440 | A1 | 7/2005 | Kanjilal et al. |
| 2005/0228310 | A1 * | 10/2005 | Pfistershammer ... A01K 11/002 600/567 |
| 2005/0256425 | A1 | 11/2005 | Prusiner et al. |
| 2006/0021673 | A1 | 2/2006 | Rodewald |
| 2007/0103314 | A1 | 5/2007 | Geissler |
| 2007/0142743 | A1 | 6/2007 | Provencher et al. |
| 2007/0239067 | A1 | 10/2007 | Hibner et al. |
| 2007/0293826 | A1 | 12/2007 | Wall et al. |
| 2008/0044313 | A1 | 2/2008 | Caisley |
| 2008/0064983 | A1 | 3/2008 | Stromberg et al. |
| 2008/0222930 | A1 | 9/2008 | Pennington et al. |
| 2008/0227662 | A1 | 9/2008 | Stromberg |
| 2008/0228105 | A1 | 9/2008 | Howell et al. |
| 2009/0131825 | A1 | 5/2009 | Burbank |
| 2009/0326548 | A1 * | 12/2009 | Nehls .................. A01K 11/003 606/116 |
| 2010/0016758 | A1 | 1/2010 | Hilpert |
| 2010/0325926 | A1 | 12/2010 | Hilpert et al. |
| 2011/0295148 | A1 | 12/2011 | Destoumieux et al. |
| 2012/0010526 | A1 | 1/2012 | Hilpert et al. |
| 2013/0175347 | A1 | 7/2013 | Decaluwe et al. |
| 2013/0195542 | A1 | 8/2013 | Decaluwe et al. |
| 2013/0204159 | A1 | 8/2013 | Destoumieux et al. |
| 2013/0211287 | A1 | 8/2013 | Decaluwe et al. |
| 2013/0211416 | A1 | 8/2013 | Teychene et al. |
| 2014/0083367 | A1 | 3/2014 | Kellerby et al. |
| 2014/0249449 | A1 | 9/2014 | Hilpert et al. |

FOREIGN PATENT DOCUMENTS

| | | |
|---|---|---|
| EP | 0212885 | 9/2001 |
| EP | 1504722 | 2/2005 |
| EP | 1759638 A1 | 3/2007 |
| EP | 1772104 | 4/2007 |
| EP | 1911347 A1 | 4/2008 |
| EP | 2191715 A1 | 6/2010 |
| FR | 2831389 A1 | 5/2003 |
| FR | 2917574 A1 | 12/2008 |
| FR | 2924899 A1 | 6/2009 |
| FR | 2939281 A1 | 6/2010 |
| FR | 2961088 A1 | 12/2011 |
| FR | 2963203 A1 | 2/2012 |
| FR | 2963536 A1 | 2/2012 |
| FR | 2963722 A1 | 2/2012 |
| FR | 2978328 A1 | 2/2013 |
| FR | 2961087 B1 | 6/2013 |
| FR | 2940011 B1 | 11/2014 |
| GB | 2358061 A | 7/2001 |
| JP | 2006026227 A | 2/2006 |
| WO | 199626675 A1 | 9/1996 |
| WO | 200189388 A1 | 11/2001 |
| WO | 2002039810 A2 | 5/2002 |
| WO | 2002078431 A2 | 10/2002 |
| WO | 2004/010773 | 2/2004 |
| WO | 2005110602 A1 | 11/2005 |
| WO | 2006000869 A2 | 1/2006 |
| WO | 2006045162 A2 | 5/2006 |
| WO | 2007087261 A2 | 8/2007 |
| WO | 2007087355 A2 | 8/2007 |
| WO | 2008003693 A1 | 1/2008 |
| WO | 2008043156 A1 | 4/2008 |
| WO | 2008055690 A1 | 5/2008 |
| WO | 2008152980 A1 | 12/2008 |
| WO | 2009074659 A1 | 6/2009 |
| WO | 2009076469 A1 | 6/2009 |
| WO | 2009089215 A1 | 7/2009 |
| WO | 2009149716 A1 | 12/2009 |
| WO | 2010063287 A1 | 6/2010 |
| WO | 2010066475 A1 | 6/2010 |
| WO | 2010070130 A2 | 6/2010 |
| WO | 2011047902 A1 | 4/2011 |
| WO | 2011154233 A1 | 12/2011 |
| WO | 2011154510 A1 | 12/2011 |
| WO | 2012013429 A1 | 2/2012 |

(56) References Cited

FOREIGN PATENT DOCUMENTS

| WO | 2012019911 A1 | 2/2012 |
|---|---|---|
| WO | 2012019956 A1 | 2/2012 |
| WO | 2013014034 A1 | 1/2013 |

OTHER PUBLICATIONS

French International Search Report for Application 1056600, Dated Mar. 2011, 2 pgs.
International Preliminary Report on Patentability for International Application No. PCT/EP2008/067354, Report dated Aug. 3, 2010, 12 Pgs.
International Preliminary Report on Patentability for International Application No. PCT/EP2009/059981, Report dated Jun. 14, 2011, 12 Pgs.
International Preliminary Report on Patentability for International Application No. PCT/EP2009/067591, Report dated Aug. 2, 2011, 14 Pgs.
International Preliminary Report on Patentability for International Application No. PCT/EP2011/058106, Report dated Dec. 10, 2012, 7 Pgs.
International Preliminary Report on Patentability for International Application No. PCT/EP2011/059636, Report dated Dec. 10, 2012, 11 Pgs.
International Preliminary Report on Patentability for International Application No. PCT/EP2011/060558, Report dated Feb. 5, 2013, 8 Pgs.
International Preliminary Report on Patentability for International Application No. PCT/EP2011/062896, Report dated Feb. 19, 2013, 5 Pgs.
International Preliminary Report on Patentability for International Application No. PCT/EP2011/063407, Report dated Feb. 12, 2013, 7 Pgs.
International Preliminary Report on Patentability for International Application No. PCT/EP2012/064018, Report dated Jan. 28, 2014, 11 Pgs.
International Search Report and Written Opinion for International Application No. PCT/EP2009/067591, Search completed Nov. 25, 2010, dated Dec. 2, 2010, 9 Pgs.
International Search Report and Written Opinion for International Application PCT/EP2009/059981, completed Nov. 6, 2009, dated Nov. 13, 2009, 9 pgs.
International Search Report for Application PCT/EP2008/067354, report completed Apr. 21, 2009, dated Apr. 28, 2009, 6 pgs.
International Search Report for International Application. PCT/EP2012/064018, Search Completed Oct. 4, 2012, dated Oct. 15, 2012, 3 pgs.
International Search Report for International Application PCT/EP2011/063407, Search completed Oct. 31, 2011, dated Nov. 10, 2011, 5 Pgs.
Preliminary Search Report for Application No. FR 1056349, dated Mar. 4, 2011, 2 pgs.
Search Report and Written Opinion for International Application PCT/EP2011/059636, completed Jul. 5, 2011, dated Jul. 19, 2011, 13 pgs.
Search Report for French Application 1054563, dated Jan. 13, 2011, 2 pages.
Written Opinion for International Application No. PCT/EP2012/064018, Search Completed Oct. 4, 2012, dated Oct. 15, 2012, 10 pgs.
Written Opinion for International Application PCT/EP/2008/067354, 10 pgs.
"Academic press Dictionary of science and technology", Translation. (1992). In C. Morris (Ed.) Oxford, United Kingdom: Elsevier Science & Technology. Retrieved from <http://search.credoreference.com/content/entry/apdst!translation/0> on Feb. 23, 2016.
French International Search Report for Application 1056520, Dated Apr. 14, 2011, 2 pgs.
International Search Report and Written Opinion for International Application PCT/EP2011/062896, Report dated Sep. 16, 2001, 7 pgs.
International Search Report for International Application No. PCT/EP2011/058106, Search completed Jul. 4, 2011, dated Jul. 13, 2011, 5 pgs.
Search Report for French application 1054564, 2 pgs.
Written Opinion for International Application PCT/EP2011/058106, 11 pgs.
Written Opinion for International Application PCT/EP2011/063407, Search completed Oct. 31, 2011, dated Nov. 10, 2011, 6 Pgs.

* cited by examiner

UNIT FOR MARKING AND/OR SAMPLING ANIMAL TISSUE AND CORRESPONDING MARKING AND/OR SAMPLING TOOL

1. FIELD OF THE INVENTION

The field of the invention is that of the identifying and/or collecting of tissue from animals.

More specifically, the invention pertains to a novel unit for tagging and/or collecting tissue from an animal, making it possible especially to protect the male or female parts of a tagging and/or collecting device before they are used and to facilitate their installation on a corresponding tagging and/or collecting tool.

2. PRIOR ART

The identification of livestock has been compulsory in many countries in order to ensure the tracking of livestock and guarantee the origin of animals intended especially for consumption.

Thus, in order to ensure its traceability, an animal is classically identified by means of a visual and/or electronic marking device also called a tag. Such a tag is made by a male tagging portion and a female tagging portion designed to be irreversibly associated.

For example, in the context of animal identification, the male part comprises a rod which extends from a support designed to rest on a surface of the animal's ear. The end of the rod terminates in a conical or truncated conical tip, also called a head, demarcating an external shoulder enabling the tip to be held in a cavity for receiving the female part. Such a tip is used to perforate the animal's ear before the male part and the female part are associated.

There is also a known way of collecting animal tissue when applying a tag or else independently of the applying of the tag.

For example, when this collecting is done while applying a tag, the tip can be truncated and enable the passage of a biopsy needle type of collecting element. In one variant, a punch type of collecting element can be provided at the end of the truncated tip.

When this collecting is done independently of the applying of the tag, a punch type of collecting element can be fixed to a collecting tool such as a set of pliers for example.

In all these applications (the marking or tagging of the animal and/or the collecting of tissues from the animal), several elements have to be handled in order to be able to apply the tag or collect a sample of tissue.

Thus, to place a tag on an animal, it is necessary to mount the male tagging part on a first arm of a tagging tool, mount the female tagging part on a second arm of the tagging tool, and if necessary dip the unit in disinfectant before the tagging operation can be performed.

To collect a sample of animal tissue and simultaneously place a tag, it is necessary to mount the male tagging and collecting part (comprising a rod and a collecting element) on a first arm of a tagging and collecting tool, mount the female tagging and tissue-receiving part on a second arm of the tagging and collecting tool, and if necessary dip the unit in disinfectant before the tagging and collecting operations can be performed.

To collect a sample of animal tissue without simultaneously placing a tag, it is necessary to mount the male collecting part (comprising a collecting element) on a first arm of the collecting tool, mount the female tissue-receiving part on a second arm of the collecting tool, and if necessary dip the unit in a disinfectant before the collecting operation can be performed.

These operations for mounting different elements on the tagging and/or collecting tool are painstaking for the user.

There is therefore a risk that an element to be mounted on the tool may get dropped and either get lost or be contaminated by the external environment (through dust, moisture, bacteria, etc).

In addition, there is an increased risk that the user might get injured during the handling of these different elements, especially the handling of the collecting element or the tip of the male part.

There is therefore a need for a novel packaging of these elements which would simplify their assembly.

3. SUMMARY OF THE INVENTION

The invention proposes a novel solution in the form of a unit for tagging and/or collecting tissue from an animal comprising:

a male part for tagging and/or collecting tissue, a female part for tagging and/or receiving said tissue.

According to the invention, such unit comprises an intermediate linking element between the male and female parts, said intermediate linking element having a first portion for joining to said male part and a second portion for joining to said female part enabling said male and female parts to be held in a same tagging and/or collecting axis, prior to the tagging and/or collecting of tissue from said animal, said intermediate linking element being removable. In particular, the first joining portion comprises at least one housing receiving at least partially the male part. The invention thus proposes a "one-piece" assembly in which the male part for tagging and/or collecting tissue and the female part for tagging and/or receiving tissue are held coaxially prior to the operation of being mounted on a tagging and/or collecting tool.

In other words, the male part, the intermediate linking part and the female part have a same axis which extends in only one direction (which may be slightly curved). The intermediate linking element therefore offers a rigid link providing for alignment between the male and female parts.

The use of an intermediate linking element according to the invention has numerous advantages.

First of all, the intermediate linking element enables the male part and the corresponding female part to be held together prior to the identification and/or collection of the animal tissue. In this way, the intermediate linking part facilitates the transportation and handling of the male and female parts. In addition, the risks of error that may arise in using a male part and a female part that do not correspond to it (that do not have the same identifier for example) are reduced. Finally, the pre-assembly (in the mounting position) of the male and female parts simplifies the mounting of the different elements on the tagging and/or collecting tool since it is only the one-piece assembly that has to be handled.

Besides, the intermediate linking element enables the male and/or female parts to be protected. In particular, this linking element protects the tip or the collecting element from the external environment (dust, moisture, bacteria, etc). In particular, it protects the tip or the collecting element (especially its cutting edge) against deterioration and fouling. Thus, a high quality of perforation by the tip or of cutting by the collecting element is maintained. Furthermore, the use of such an intermediate linking element prevents the user from getting injured during the handling of the tip or the collecting element.

To this end, in a first aspect, the first joining portion covers at least one tip and/or the end of a collecting element of the male part.

For example, the housing or housings of the first joining portion at least partially receive the tip and/or the collecting element, the input hole of the housing comprising at least one ledge enabling the tip and/or the collecting element to be held in the intermediate linking element.

Thus, the male part can be fitted into the intermediate linking element to join the male tagging and/or collecting part and the intermediate linking element. It is also possible to protect the tip and/or the collecting element during handling operations prior to the tagging and/or collecting through the intermediate linking element and then (by hand or automatically) withdraw the intermediate linking element once the male part and the female part are mounted on the tagging and/or collecting tool.

According to a second aspect, the second joining portion is inserted into a collecting tube and/or a receiving cavity of the female part.

Thus, the intermediate linking element can be fitted into the female tagging and/or receiving part to join the female part and the intermediate linking element. This also protects the female part, in preventing foreign bodies from getting housed in the receiving cavity or in the collecting tube of the female part. It is thus not necessary to close a tube of this kind with a lid prior to the collecting operation.

To this end, according to one particular embodiment, the second joining portion is cylindrical and has a diameter slightly smaller than the diameter of the collecting tube and/or the receiving cavity of the female part.

According to one variant, the second joining portion covers the open end of a collecting tube or a tube head.

According to this variant, pertaining more specifically to the collecting operations, a tube or a tube head can be nested into the intermediate linking element to join the female collecting part and the intermediate linking part.

Advantageously, the male part, the intermediate linking part and the female part have a shape generated by revolution around a same axis of revolution.

According to another aspect, the intermediate linking part is at least partially deformable.

In this way, it is easier to put it in place during the manufacturing of the unit and to remove it before the tagging and/or collecting operation.

For example, the intermediate linking element is made out of a slightly deformable plastic material such as polypropylene (PP), polystyrene (PS), polyethylene (PE) or else again a biodegradable plastic such as polylactide (PLA) or starch (PCL). It can be noted that the geometry of the intermediate linking element can be adapted in order to facilitate its deformation.

According to one particular embodiment, the intermediate linking element is a set of pliers comprising at least one moving part.

The male and female parts are then held together by the moving parts of the pliers.

In particular, a set of pliers of this kind comprises grasping means forming a lever enabling the moving part or parts of the pliers to be actuated.

It is thus easy to handle the unit, install it on the tagging and/or collecting tool and detach the male and female parts through these grasping means.

Advantageously, the intermediate linking part contains a specific agent to be applied at least partially to the male part and/or to the female part such as: a disinfectant, a cicatrizing agent, a preserving agent, a desiccant, a medicine, a vaccine, a combination of at least two of the foregoing agents.

Thus, for example, the tip or the collecting element of the male part is in contact with the disinfectant or antiseptic when it is housed in the intermediate linking element. In addition to protecting the user from the tip or the cutting edge of the collecting element, this aspect disinfects the male part before use, thus reducing the risk of contamination of the animal's wound and enabling improved healing.

In particular, an agent of this kind may take different forms such as a gel, a cream, a grease, a liquid, a powder, a gas, an impregnated foam, etc.

The invention also pertains to a tool for tagging and/or collecting tissue from an animal, provided in order to cooperate with a unit as described here above.

According to the invention, such a tool comprises means for disjoining said male part and said female part.

Thus, once the unit is mounted on one of the arms by means of the male part or the female part, the tool according to the invention enables the other part on the other arm to be "retrieved" without the user's having to handle the unit.

According to one particular embodiment, the means for disjoining (or detaching or disconnecting) comprise means for locking said female part to said tool enabling said unit to be fixedly joined to said tool.

For example, these locking means are means of a type such as a lock ring, a translating element, a pedal, etc.

According to this particular embodiment, the disjoining means also comprise hooking means activated by action on said tool, enabling said male part to be fixedly joined to said tool and enabling said male part to be disjoined from said intermediate linking tool or said female part.

For example, these hooking means are clamping, clip-on and other types of means.

Thus, in a first stage, the unit is mounted on an arm of the tool and, in a second stage, the tool is actuated enabling the male and female parts to be disjoined.

According to another characteristic, the tool comprises means for ejecting the intermediate linking element.

In this way, the user does not have to handle the intermediate linking element, thus again preventing the risk of injury or of contamination of the tip or the collecting element.

4. LIST OF FIGURES

Other features and advantages of the invention shall appear more clearly from the following description of a particular embodiment, given as a simple illustratory and non-exhaustive example and from the appended figures, of which:

5. DESCRIPTION OF ONE EMBODIMENT OF THE INVENTION

5.1 General Principle

The general principle of the invention relies on the use of an intermediate linking element enabling a male part for tagging and/or collecting tissue to be joined to a female part for tagging and/or receiving tissue, prior to the tagging and/or collecting operations.

In this way, the handling, transportation, etc of the male and female parts and their mounting on a tagging and/or collecting tool are facilitated.

More specifically, an intermediate linking element of this kind provides for a rigid or semi-rigid link between the male and female parts and therefore maintains these male and female parts in a same alignment.

Here and here below, the term "male part" is understood to mean:
- a male part formed by a rod extending from a support and terminating in a tip if the context is one of animal tagging (the applying of a visual and/or electronic tag),
- a biopsy needle type or punch type collecting element if the context is one of the collecting of animal tissue (collecting done independently of the applying of a visual and/or electronic tag),
- a male part comprising a rod extending from a support and comprising a biopsy needle type or punch type collecting element if the context is one of tagging and collecting animal tissue (collecting done jointly with the applying of a visual and/or electronic tag);

and the term "female part" is understood to mean:
- a female part comprising a receiving cavity if the context is one of animal tagging,
- a collecting tube if the context is one of the collecting of animal tissue,
- a female part comprising a receiving cavity and/or a collecting tube if the context is one of tagging and collecting animal tissue.

5.2 Application to Animal Tagging

Here below, referring to FIGS. 1A to 1C, we refer to a first example of a unit 11 according to the invention that can be used in the context of animal tagging (applying a visual and/or electronic tag).

Figure 1A:
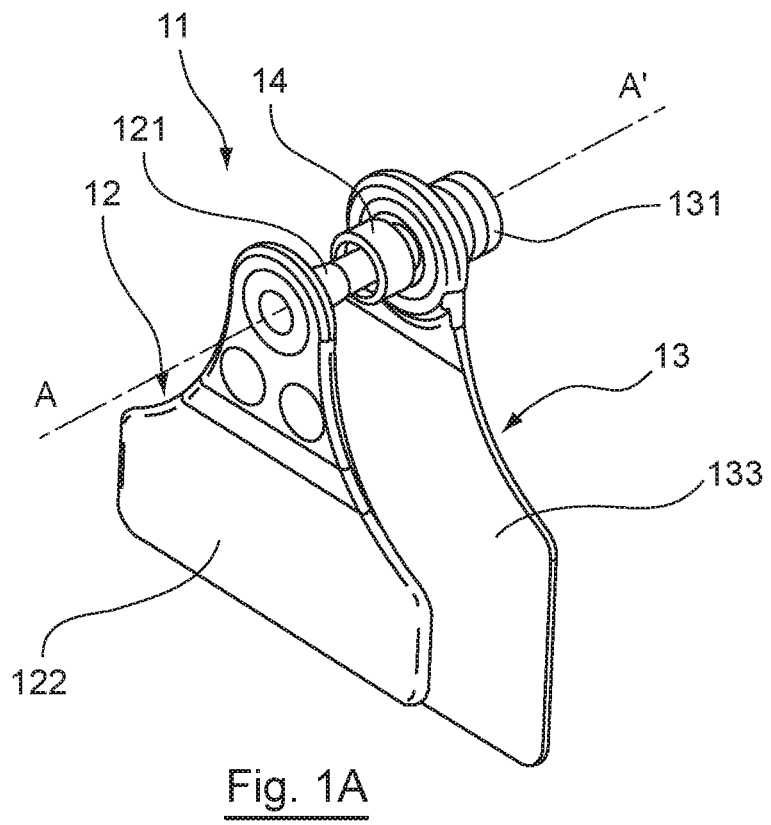
FIGS. 1A to 1C illustrate a first example of a unit according to the invention that can be used to tag or mark an animal.

As illustrated in FIG. 1A, such a unit 11 comprises a male part 12, a female part 13 and an intermediate linking part 14.

The male part 12 and female part 13 are classic.

For example, the male part 12 has a rod 121 extending from a marking support 122. The rod 121 is terminated by a conical or truncated conical tip 123 (also called a head) demarcating an external shoulder 124 at its base. The tip 123 is used to perforate the animal's skin before the male part 12 is associated with the female part 13.

The female part 13 for its part has a receiving button 131 with a cavity 132 for the introduction of the tip 123 of the rod 121. Strips 134 are provided at the inlet orifice of the cavity 132 enabling the tip 123 to pass in one sense in order to insert the tip 123 of the male part into the cavity 132 and prevent it from being extracted in the other sense.

The base of the female part also forms a marking support 133.

According to the invention, the male part 12 and the female part 13 are held coaxially along the tagging axis AA' through the intermediate linking element 14. In other words, the intermediate linking element enables the male part 12 and the female part 13 to be joined so that the axis of revolution of the rod 121 and the axis of revolution of the receiving cavity 132 coincide.

Figure 1B:
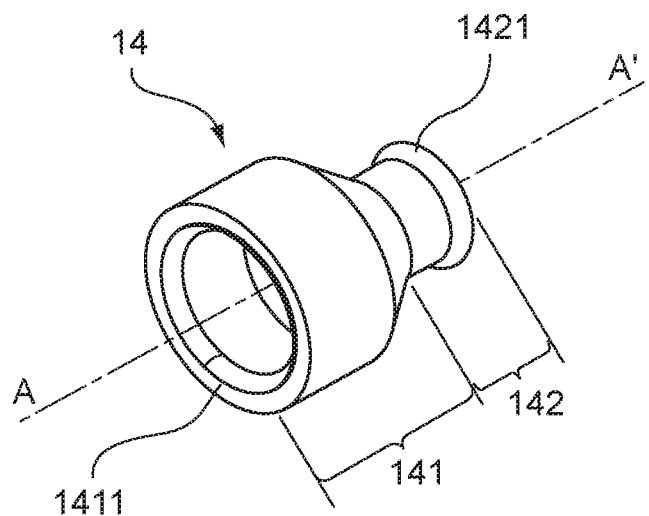

More specifically, as illustrated in FIG. 1B, the intermediate linking element 14 has a first portion 141 for joining to the male part 12 and a second portion 142 for joining to the female part 13 enabling the male and female parts to be held together prior to the tagging of the animal.

Figure 1C:
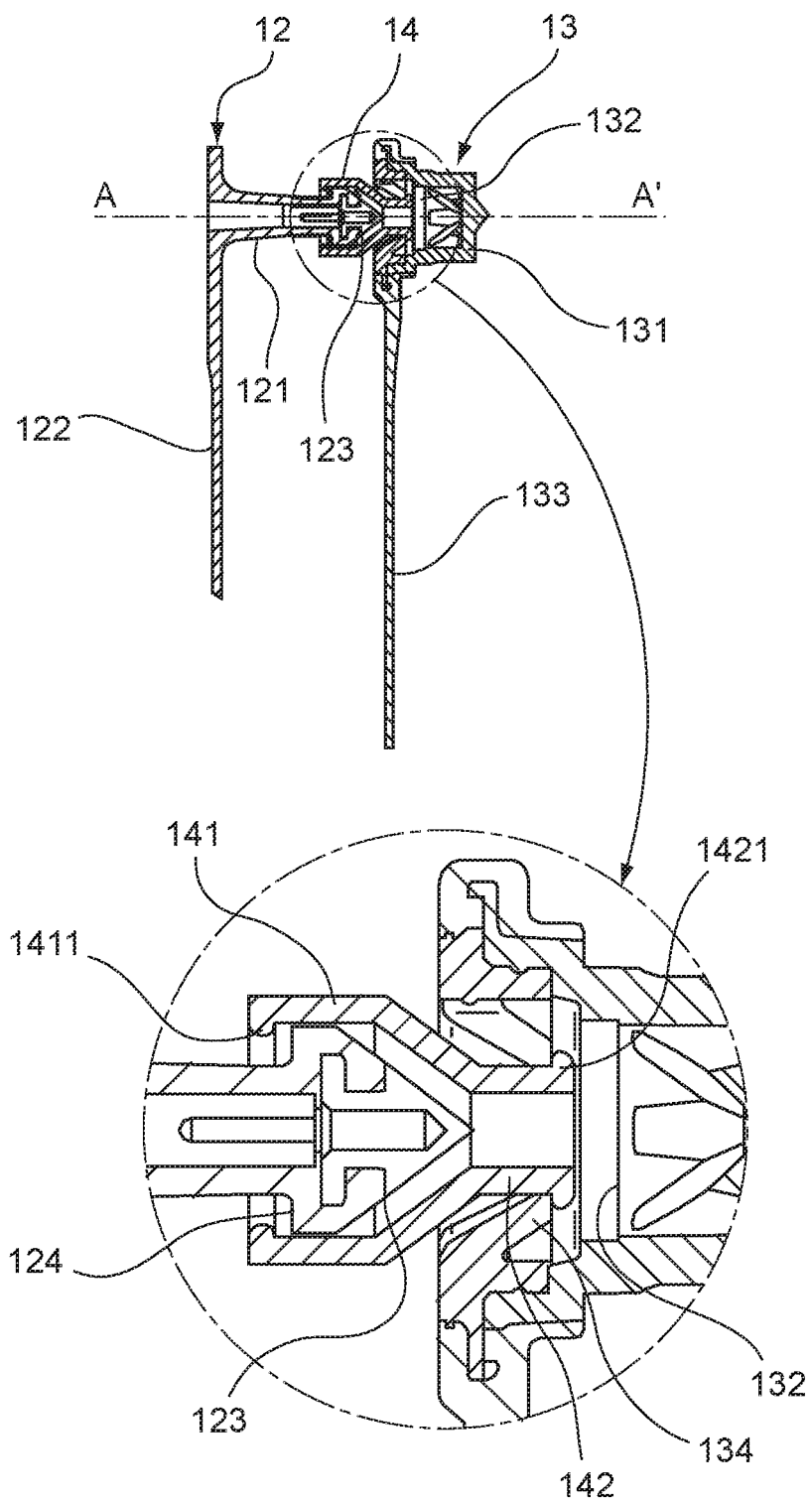

According to this example, and as illustrated in FIG. 1C, the first joining portion 141 covers the tip 123 of the male part 12. More specifically, the first joining portion 141 defines a housing having a shape suited to receiving the tip 123. The internal diameter of the housing is therefore slightly greater than that of the base of the tip 123 (corresponding to the widest part of the tip) so that it can penetrate the housing. Furthermore, the inlet hole of the housing comprises at least one inner ledge 1411 enabling the tip 123 to be held in the intermediate linking element 14, the shoulder 124 of the tip 123 abutting the inner ledge 1411 when the tip 123 is inserted in the intermediate linking element. In this way, the linking element protects the tip from the external environment (dust, moisture, bacteria, etc).

The second joining portion 142 for its part is inserted into the receiving cavity 132 of the female part 13. More specifically, the second joining portion 142 has a shape adapted to cooperating with the receiving cavity 132. It is for example cylindrical and has a diameter slightly smaller than the diameter of the receiving cavity 132 of the female part. It also has at least one outer ledge 1421 used to hold the intermediate linking part 14 in the cavity of the female part, the strips 134 of the female part taking support on the outer ledge 1421 to hold the intermediate linking element 14 in the female part. Advantageously, the diameter of the base of the tip 123 is greater than the diameter of the outer ledge 1421 of the second joining portion 1421 so as not to cause deterioration in the strips 134 during the withdrawal of the intermediate joining element 14 from the female part.

The intermediate linking part 14 or the inner ledge 1411 and outer ledge 1421 can be made out of a slightly deformable material such as polypropylene, polystyrene, polyethylene, in order to facilitate the insertion and the withdrawal of the male part 12 into and from the first joining section 141 and the insertion and withdrawal of the second joining section 142 into and from the female part 13. The intermediate linking element 14 must also be rigid enough to hold the male part and the female part coaxially, especially during the transportation of the unit and its positioning on the tagging tool.

It may be recalled that the intermediate linking element 14 is removable. It can therefore be withdrawn just before the operation for tagging the animal. It is then necessary to exert a slight force to release the male part 12 and female part 13 from the linking element 14.

More advantageously, a specific agent is provided within the intermediate linking element 14. It may be a disinfectant, a cicatrizing agent, a medicine, a vaccine, etc. Such an agent thus makes it possible to at least partially destroy the microorganisms (bacteria, viruses, etc) that might cause infection in the tissues perforated during the tagging or to heal or treat the animal if need be, this agent being capable of passing into the blood at the perforated tissues or being absorbed by the animal's skin.

In particular, a specific agent of this kind may take different forms such as a gel, a cream, a grease, a liquid, a powder, a gas, an impregnated foam, etc. possibly contained in a reservoir or closed by a lid which will be pierced by the tip of the male part.

5.3 Application to Collection Combined with Tagging

Here below, referring to FIGS. 2A to 2D, we describe a second example of a unit 21 according to the invention that can be used in a context of tagging and collecting animal tissue.

Figure 2A:
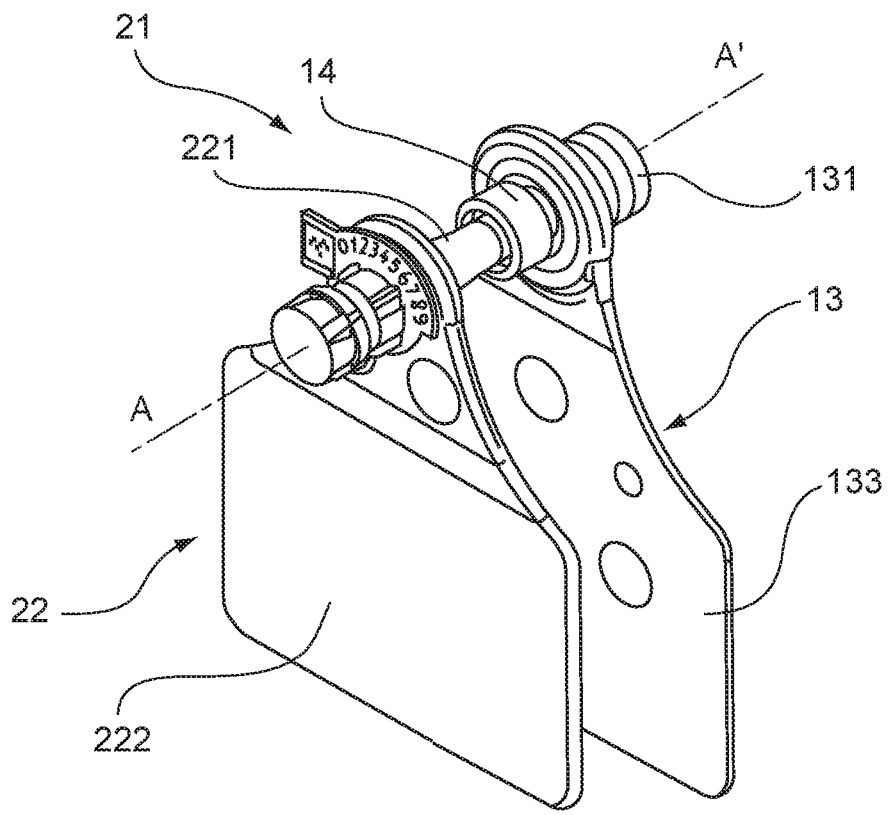
FIGS. 2A to 2D illustrate a second example of a unit according to the invention that can be used to tag an animal and simultaneously collect a sample of animal tissue.

As illustrated in FIG. 2A, a unit 21 of this kind has a male part 22, a female part 13 and an intermediate linking part 14.

According to this example, the male part 22 has a rod 221 extending from a marking support 222. The rod 221 is terminated by a conical or truncated conical tip 23 that is truncated, demarcating an external shoulder 224 at its base. The rod 223 enables the passage of an element for collecting animal tissue such as a biopsy needle 225 or a punch.

The female part 13 can be similar to the female part described with reference to FIGS. 1A and 1B.

According to the invention, the male part 22 and the female part 13 are held coaxially along the tagging and collecting axis AA' through the intermediate linking element 14. In other words, the intermediate linking element enables the male part 22 and female part 13 to be joined so that the axis of revolution of the rod 221 and the axis of revolution of the receiving cavity 132 coincide.

The intermediate linking element 14 is similar to the one described with reference to FIGS. 1A to 1C. More specifically, as illustrated in FIGS. 1B and 1C, the first joining portion 141 covers the truncated tip 223 of the male part 22 and the end of the collecting element 225. The first joining portion 141 herein defines a housing with a shape appropriate to receiving the tip 223 and the end of the collecting element 225.

Thus, the intermediate linking element 14 protects the tip and the collecting element against deterioration and fouling. Thus, the invention preserves high quality of cutting by the cutting edge of the collecting element.

Figure 2B:
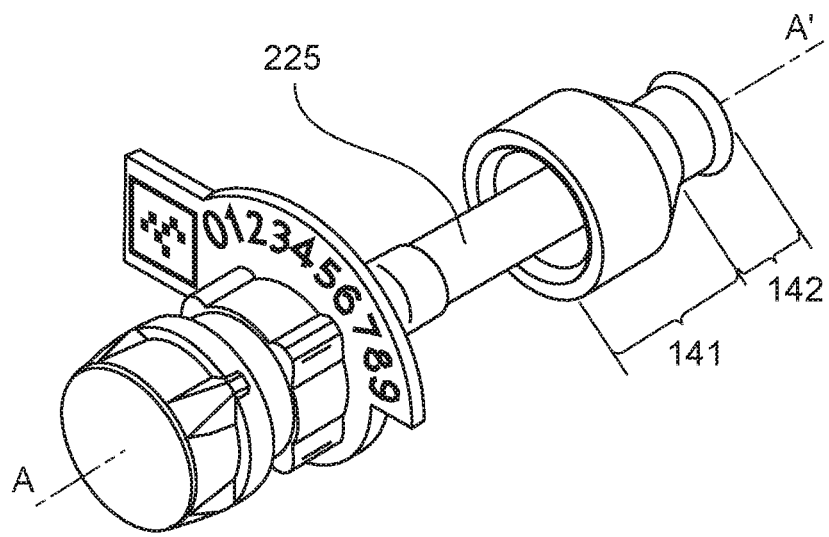
Figure 2C:
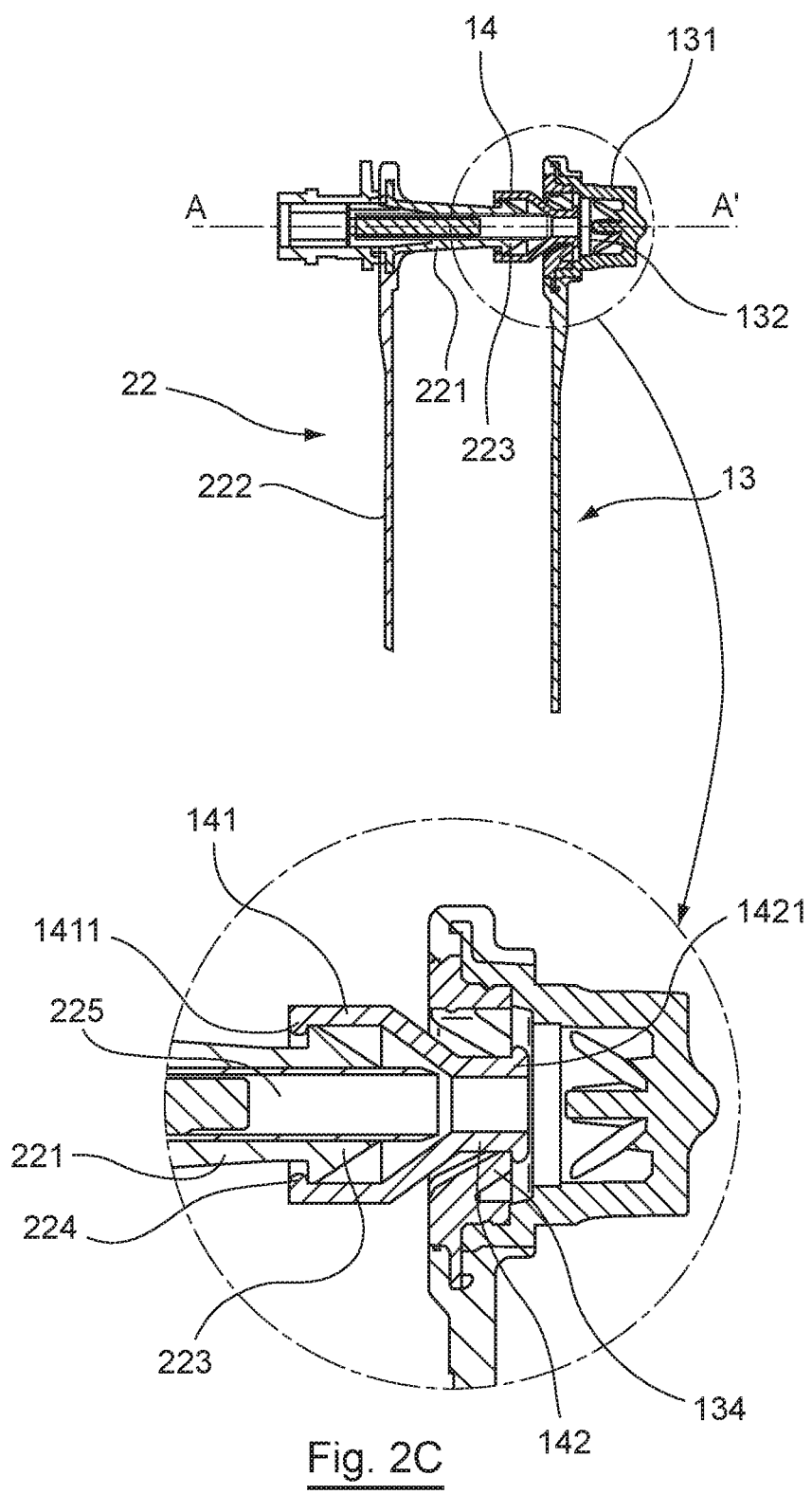
Figure 2D:
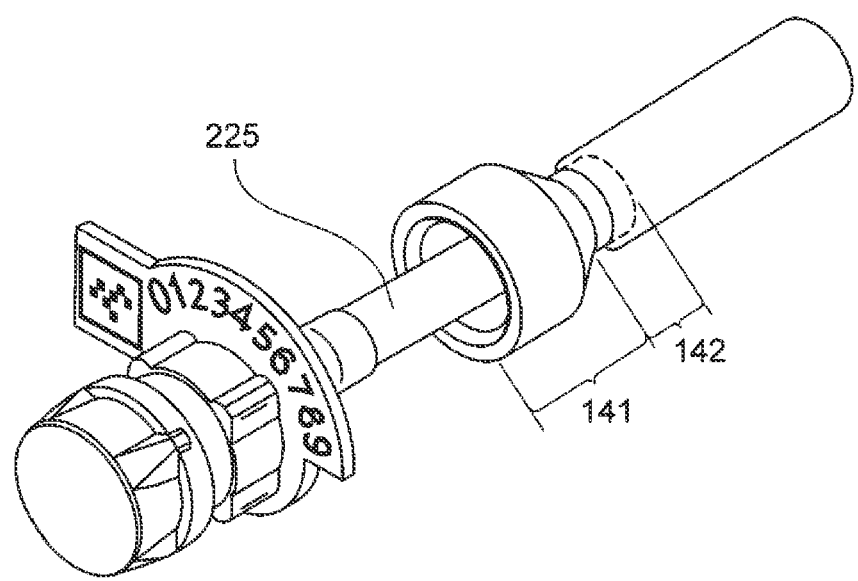

As indicated here above, a specific agent can be provided within the intermediate linking element 14. Thus, as illustrated in FIG. 2B, the cutting edge of the collecting element can be in contact with a disinfectant, cicatrizing agent, etc. before the collecting operation.

In a context of tagging and collecting, such an agent can also be a preserving agent or desiccant making it possible to improve the preservation of a sample of tissue to be collected and possibly to prepare it with a view to subsequent treatment such as DNA analysis.

In other words, the specific agent according to the invention can take the form of any product capable of acting on the animal or on a sample of tissue collected from the animal.

5.4 Application to Collecting

Here below, referring to FIGS. 3A to 3C, we describe a third example of a unit 31 according to the invention which can be used in a context of collecting animal tissue (implemented independently of the applying of a visual and/or electronic tag).

Figure 3A:
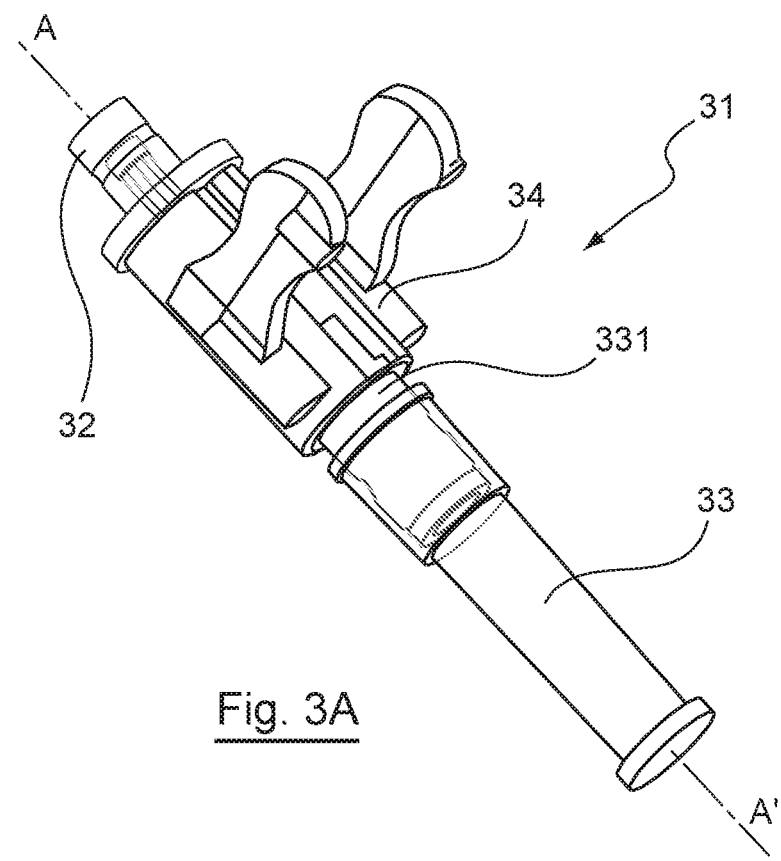
FIGS. 3A to 3C illustrate a third example of a unit according to the invention that can be used to collect a sample of animal tissue independently of the applying of an identification tag.

As illustrated in FIG. 3A, a unit 31 of this kind has a male part 32 comprising a collecting element, a female part 33 comprising a collecting tube and an intermediate linking element 34.

For example, the collecting element comprises a cutting element 321 designed to cut a sample of tissue from the animal and a pushing element 322 that is movable relatively to the cutting element 321, enabling the sample to be pushed into a collecting tube 33 after the sample has been cut out by the cutting element 321.

The collecting tube 33 for its part is equipped with a tube head 331. In particular, a tube head of this kind provides a support on which the cutting element 321 can press in order to accurately cut the animal's tissues. It also enables the closing of the tube, for example by fitting or clipping the pushing element 322 and/or the cutting element 321 into the tube head 331, as well as enabling the automation of the opening of the tubes by the analysis laboratories, in opening the tube head so that the sample remains inside the tube.

A collecting element and a collecting tube according to this third example are described especially in the French patent application FR 2 939 281 filed on behalf of the present Applicant.

According to the invention, the male part (the collecting element) 32 and the female part (the collecting tube) 33 are held coaxially along the collecting axis AA', through the intermediate linking element 34. In other words, the intermediate linking element enables the male part 32 and female part 33 to be joined so that the axis of revolution of the collecting element 32 and the axis of revolution of the collecting tube 33 coincide.

Figure 3B:
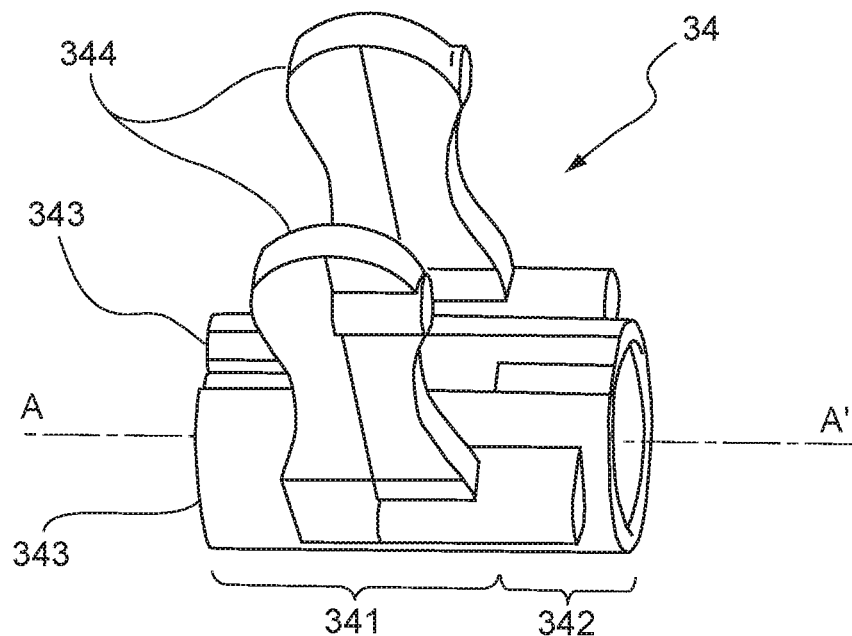

More specifically, as illustrated in FIG. 3B, the intermediate linking element 34 has a first portion 341 for joining to the male part 32 and a second portion 342 for joining to the female part 33 enabling the male and female parts to be held together preliminarily to the collection of animal tissue.

Figure 3C:
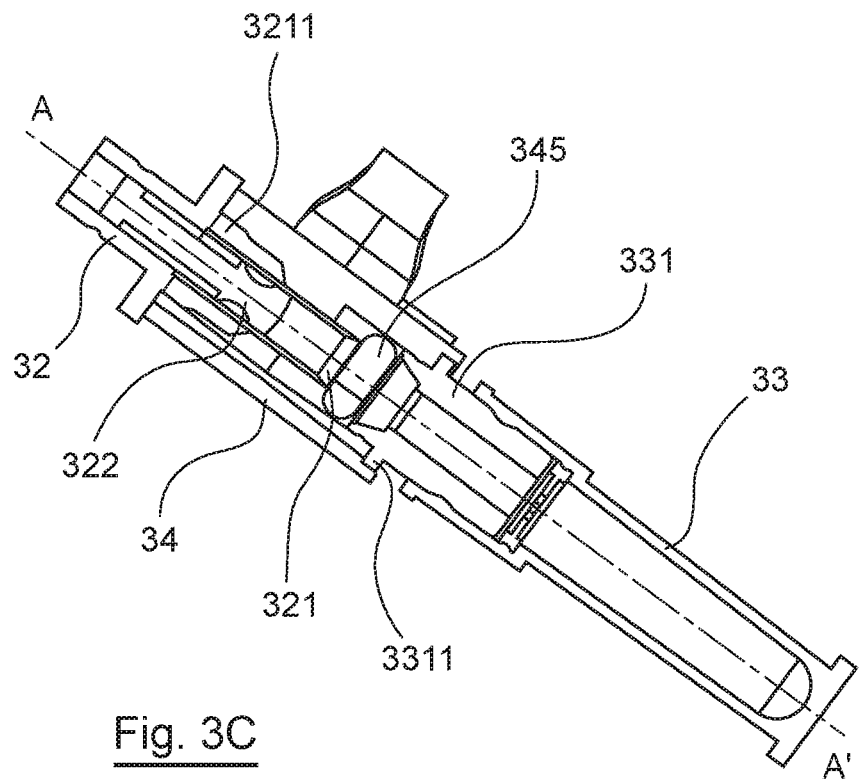

According to this example, and as illustrated in FIG. 3C, the first joining portion 341 covers the cutting element 321 of the male part 32. More specifically, the first joining portion 341 defines a housing having a shape suited to receiving the cutting element 321 and, if necessary, a part of its support 3211.

The second joining portion 342 for its part covers the open end of the collecting tube 33 or of the tube head 331. According to the example illustrated, the second joining portion 342 defines a housing with a shape adapted to receiving the tube head 331. If the tube head is provided with a collar 3311, the second joining portion can be provided with a recess to receive this collar.

In particular, according to this third example, the intermediate linking element 34 is a set of pliers comprising two moving parts 342 and grasping means 344. More specifically, the grasping means form a lever used to actuate the moving parts of the pliers. Thus, action by a user on the grasping means 344 make it possible to move the two moving parts 343 away from the pliers. It is then possible to introduce the male part 32 and the female part 33 between the moving parts 343. When the user relaxes his action, the moving parts get tightened, thus making it possible to hold the male part 32 and the female part 33 together along the collecting axis AA'. For example, each moving part takes the form of a hollow semi-cylinder, the closing of the pliers defining a cylinder at least partially encapsulating the cutting element 321 and the tube head 331.

According to this third example, the intermediate linking element 34 can be made out of a plastic such as polypropylene, polystyrene, polyethylene or else again out of a biodegradable plastic material.

Advantageously, a specific agent is provided inside the intermediate linking element 34. It may be a disinfectant, a cicatrizing agent, a preserving agent, a desiccant, a medicine, a vaccine, a combination of at least two of the above agents, etc.

For example, the specific agent is a disinfectant, impregnating a foam 345. When the clamp 34 is closed on the male part 32 and female part 33, the foam is slightly compressed and releases a disinfectant, disinfecting the cutting edge of the cutting element 321 and the inlet hole of the tube head 331.

5.5 Positioning the Unit on a Tagging and/or Collecting Tool

As already indicated, in addition to improving the safety and quality of piercing by the tip or of the cutting by the collecting element, the use of a unit according to the invention simplifies the delivery and handling of the male and female parts as well as their positioning on a tagging and/or collecting tool.

Here below, referring to FIGS. 4A to 4C, we present the different steps implemented for the positioning of the male and female parts on a collecting tool. Naturally, similar operations can be implemented for positioning on a tagging or marking tool.

For example, such a tool has a fixed part also called a body 41 defining especially a first handle and a hinged part also called a lever 42 defining a second handle.

The body 41 of the tool also defines two arms, of which a first arm 411 is to cooperate with the male part 32 and a second arm 412 that is to cooperate with the female part 33 as illustrated in FIG. 3A for example.

Figure 4A:
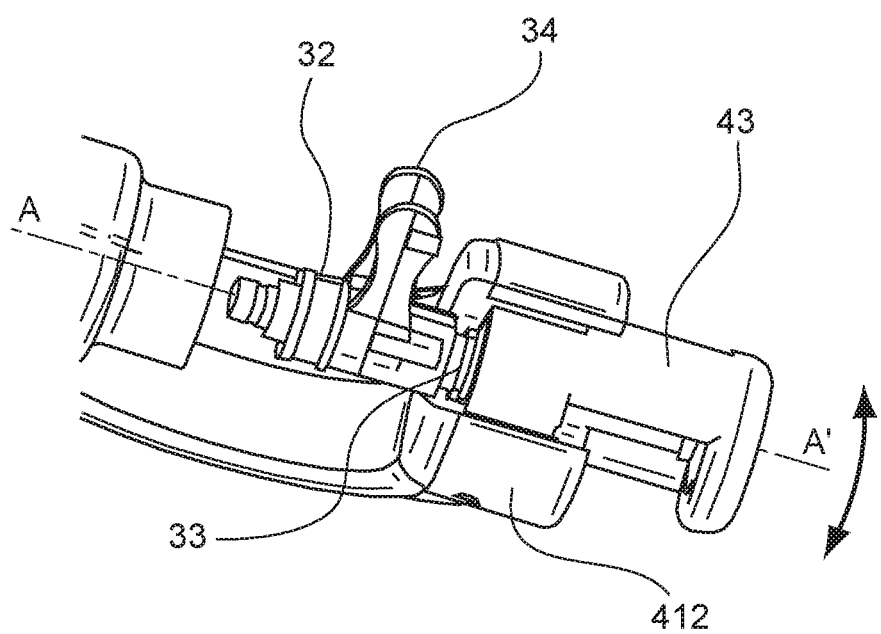
FIGS. 4A to 4C show different positions of a collecting tool during the mounting of the male and female parts of the unit on the tool.

More specifically, as illustrated in FIG. 4A, the user mounts the "one-piece" unit 31 according to the invention on the second arm 412 during a first step. It may be recalled that this unit 31 has a male part 32 formed by a collecting element, an intermediate linking part 34 and a female part 33, formed by a collecting tube comprising a tube head 31, held together along the collecting axis AA'.

To this end, the second arm 412 comprises means for locking the collecting tube 33, such as a lock ring 43 for example, enabling the unit 31 to be fixedly joined to the tool.

The male part 32, the intermediate linking part 34 and the female part 33 are then fixedly joined to the second arm 412 of the tool.

In order to separate the male part 32 and female part 33, a first action can be exerted on the collecting tool, for example on a reduced range of travel of the lever 42. In other words, the user can exert slight pressure on the lever 42 to disconnect the male part 32 and female part 33 and "set" the collecting tool. It can be noted that the tool can be actuated by hand or by means of electrical or pneumatic power or the like.

Figure 4B:
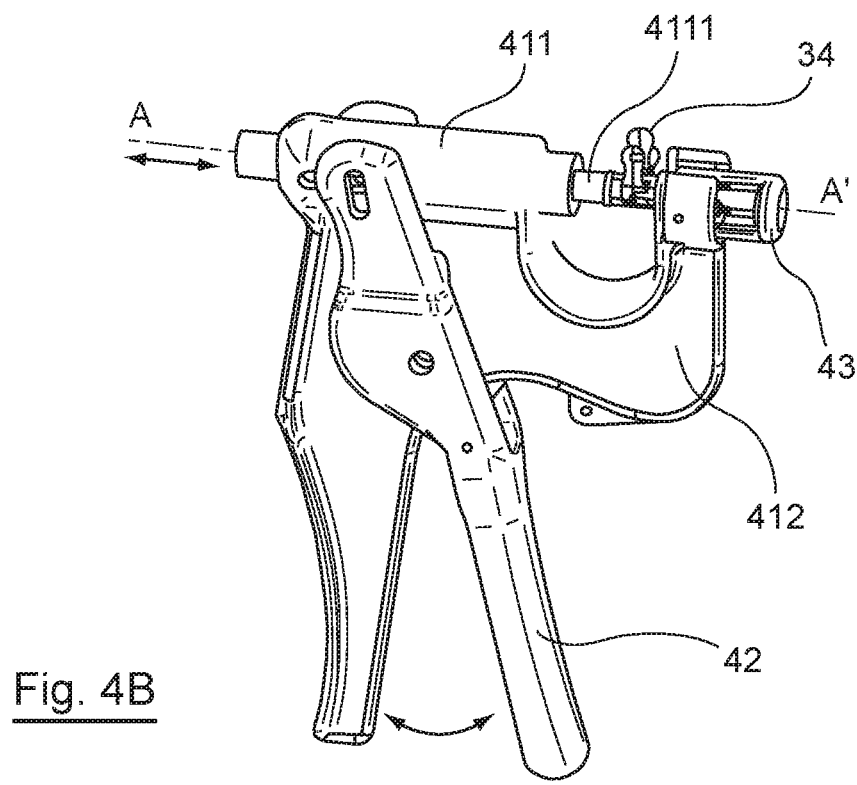

As illustrated in FIG. 4B, action on the lever 42 drives first driving means 4111. For example, these first driving means take the form of a shaft guided in translation or in rotation along the collecting axis AA'.

Such a shaft 4111 comprises hooking means used to join the male part 32 to the shaft. The shaft thus retrieves the male part 32, for example by a gripping or clip-on effect.

For example, the shaft comprises a section with a diameter slightly smaller than the inner diameter of the collecting element or of a support of the collecting element. This section with the smaller diameter can thus get inserted by force into the collecting element, at its base (its end opposite the cutting edge) to fixedly join the male part to the tool.

According to another example, the shaft comprises a portion which can expand to grip the base of the male part.

Figure 4C:
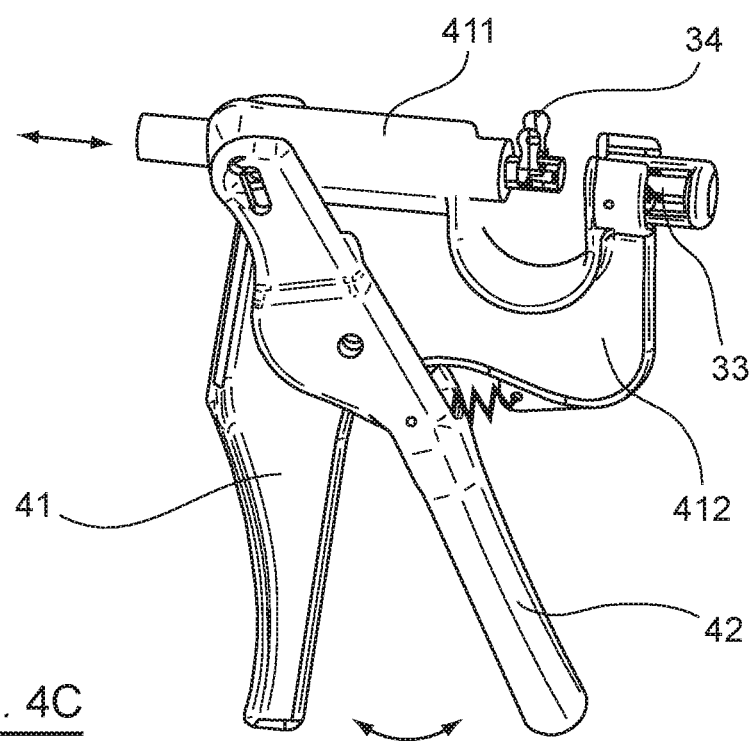

As illustrated in FIG. 4C, when the user relaxes the pressure on the lever 42 for example, the shaft 4111 returns to its initial position, driving the male part 32 with it and possibly the intermediate linking element 34. In addition to fixedly joining the male part 32 to the shaft, the hooking means thus enable the male part 32 to be detached from the intermediate linking part 34 or the female part 33.

The male part 32 and female part 33 are then both mounted on the collecting tool without the user's having had to handle the collecting element 33.

The user can then withdraw the intermediate linking element 34 which enables the cutting edge of the collecting element to be protected (in terms of safety for the user and in terms of quality for the cutting edge) in pushing on the lever-forming grasping means 344 for example, or in actuating means for ejecting the intermediate linking element provided on the tool.

For example, ejection means of this kind take the form of an independent fork-shaped lever enabling the intermediate linking element to be pushed or withdrawn and extracted from the male or female part on which it is still positioned.

The intermediate linking element 34 can then be discarded or kept so that it can, for example, be repositioned on the collecting element after the collecting operation. Such a linking element can be designed out of a biodegradable material such as polylactide (PLA) or starch (PCL).

The male part 32 and the female part 33 are then mounted respectively on each of the arms of the collecting tool, and the collecting tool is ready for the collecting operation.

A preliminary setting operation of this kind can be implemented by a collecting tool as described in the French patent application No. 1054563 filed on behalf of the present Applicant.

Figure 5A:
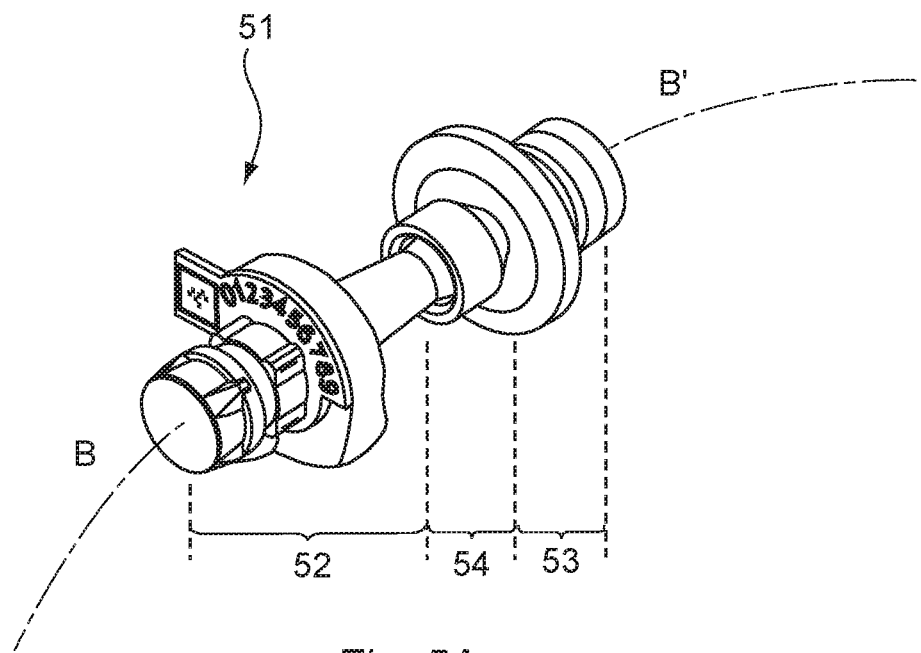
FIGS. 5A and 5B illustrate another example of a tagging and collecting tool.
Figure 5B:
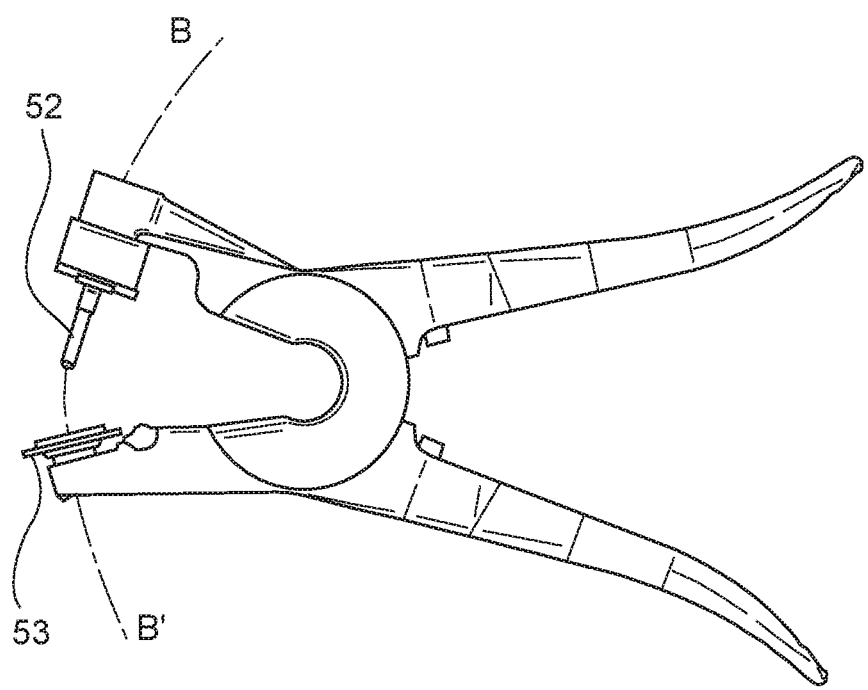

Naturally, similar operations can be implemented for a positioning on another tool such as the tagging and collecting tool illustrated in FIG. 5B for example.

In this case, as illustrated in FIG. 5A, the unit 51 comprises a male part 52 and an intermediate linking part 54 and a female part 53 held together along an axis BB' that is slightly curved to follow the tagging and collecting axis defined by the rotation of the arms of the tool.

The invention claimed is:

1. A unit for tagging and/or collecting tissue from an animal comprising:
   a male part for tagging and/or collecting tissue;
   a female part for tagging and/or receiving said tissue; and
   an intermediate linking element between said male and female parts;
   wherein said intermediate linking element comprises a first joining portion for joining to said male part and a second joining portion for joining to said female part enabling said male and female parts to be held together in a same tagging and/or collecting axis prior to the tagging and/or collecting of tissue;
   wherein said first joining portion comprises at least one housing at least partially receiving one of either a tip or an end of a collecting element of said male part;
   wherein said intermediate linking element is configured to be removed from said male part and from said female part prior to the tagging and/or collecting of tissue; and
   wherein said intermediate linking element is a set of pliers.

2. The unit according to claim 1, wherein said at least one housing comprises an input hole, where the input hole of said housing comprises at least one ledge enabling said tip and/or said collecting element to be held in said intermediate linking element.

3. The unit according to claim 1, wherein said second joining portion is inserted into a collecting tube.

4. The unit according to claim 3, wherein said second joining portion is configured to cover an open end of the collecting tube.

5. The unit according to claim 1, wherein said intermediate linking element contains a specific agent to be applied at least partially to said male part and/or to said female part.

6. The unit according to claim 5, wherein the specific agent is selected from the group consisting of a disinfectant, a cicatrizing agent, a preserving agent, a desiccant, a medicine, and a vaccine.

7. The unit of claim 1, further comprising a tool for tagging and/or collecting tissue from an animal, wherein said tool comprises means for disjoining said male part and said female part.

8. The unit of claim 7, wherein said means for disjoining comprises means for locking said female part to said tool, enabling said unit to be fixedly joined to said tool.

9. The unit of claim 7, wherein said disjoining means comprises hooking means activated by action on said tool, enabling said male part to be fixedly joined to said tool and enabling said male part to be disjoined from said intermediate linking element or said female part.

10. The unit of claim 7, further comprising means for ejecting said intermediate linking element.

11. The unit according to claim 1, wherein said second joining portion is inserted into a receiving cavity of said female part.

12. The unit of claim 1, wherein the set of pliers further comprises at least one moving part.

13. The unit according to claim 12, wherein said pliers comprise means enabling the at least one moving part to be actuated.

* * * * *